United States Patent
Imazu et al.

(10) Patent No.: US 10,197,531 B2
(45) Date of Patent: Feb. 5, 2019

(54) GATE ELECTRODE AND ION MOBILITY SPECTROMETER

(71) Applicant: SHIMADZU CORPORATION, Kyoto-shi, Kyoto (JP)

(72) Inventors: Akiko Imazu, Kyoto (JP); Hideaki Izumi, Neyagawa (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/756,137

(22) PCT Filed: May 23, 2016

(86) PCT No.: PCT/JP2016/065199
§ 371 (c)(1),
(2) Date: Feb. 28, 2018

(87) PCT Pub. No.: WO2017/038168
PCT Pub. Date: Mar. 9, 2017

(65) Prior Publication Data
US 2018/0246061 A1    Aug. 30, 2018

(30) Foreign Application Priority Data
Sep. 1, 2015    (JP) .................. 2015-171680

(51) Int. Cl.
*H01J 49/06*  (2006.01)
*G01N 27/62*  (2006.01)
*H01J 49/00*  (2006.01)

(52) U.S. Cl.
CPC .......... *G01N 27/622* (2013.01); *G01N 27/62* (2013.01); *H01J 49/0031* (2013.01); *H01J 49/06* (2013.01)

(58) Field of Classification Search
CPC ....... G01N 27/62; G01N 27/622; H01J 49/06; H01J 49/061; H01J 49/0027; H01J 49/0031; H01J 49/0036
See application file for complete search history.

(56) References Cited

U.S. PATENT DOCUMENTS

| 5,465,480 | A | * | 11/1995 | Karl | ..................... | G01N 27/622 |
| | | | | | | 29/602.1 |
| 9,123,515 | B2 | * | 9/2015 | Fujita | .................... | H01J 49/062 |

FOREIGN PATENT DOCUMENTS

| JP | 2005-174619 A | 6/2005 |
| WO | 03/065763 A1 | 8/2003 |

OTHER PUBLICATIONS

Written Opinion dated Aug. 2, 2016 in application No. PCT/JP2016/065199.
(Continued)

*Primary Examiner* — David E Smith
(74) *Attorney, Agent, or Firm* — Sughrue Mion, PLLC

(57) ABSTRACT

A gate electrode (10A) used as a shutter gate includes a pair of conductive fixture members (131, 132) made of metal and identical in size attached to the inside of a rectangular opening (12) of a ceramic base (11), along with insulating fixture members (141, 142) made of ceramic attached to the inner sides of the conductive fixture members. Two comb electrodes (151, 152) as one pair have connecting portions (151a, 152a) adhered to the conductive fixture members (131, 132) as well as thin-wire electrodes whose distal ends are adhered to the insulating fixture members (141, 142). By setting length L of the opening (12) and width D of the conductive fixture members (131, 132) to appropriate values according to the coefficient of thermal expansion of each of those members, the elongation of the electrodes which accompanies an increase in temperature can be balanced by the increase in the distance between the adhered positions of (Continued)

the electrodes to prevent the electrodes from being excessively taut or slack. Therefore, the drift region can be heated to a higher temperature than conventional levels to perform a high-accuracy, high-resolution analysis free from the influence of residual water vapor or similar particles.

4 Claims, 2 Drawing Sheets

(56) References Cited

OTHER PUBLICATIONS

Ignacio A. Zuleta, et al., "Micromachined Bradbury-Nielsen Gates", Analytical Chemistry, Dec. 1, 2007, pp. 9160-9165, vol. 79, No. 23.
International Search Report for PCT/JP2016/065199 dated Aug. 2, 2016 [PCT/ISA/210].

* cited by examiner

GATE ELECTRODE AND ION MOBILITY SPECTROMETER

CROSS REFERENCE TO RELATED APPLICATIONS

This application is a National Stage of International Application No. PCT/JP2016/065199, filed on May 23, 2016, which claims priority from Japanese Patent Application No. 2015-171680, filed on Sep. 1, 2015.

TECHNICAL FIELD

The present invention relates to a gate electrode for damming charged particles, such as ions, and for allowing those particles to pass through, as well as an ion mobility spectrometer using such a gate electrode as a shutter gate for introducing ions in a pulsed form into a drift region.

BACKGROUND ART

When a molecular ion generated from a sample molecule is made to move in a gas medium (or liquid medium) under the effect of an electric field, the ion moves at a speed proportional to its mobility which is determined by the intensity of the electric field, size of the molecule and other factors. Ion mobility spectrometry (IMS) is a measurement method in which this mobility is utilized for an analysis of sample molecules. FIG. 3 is a schematic configuration diagram of a conventional and common type of ion mobility spectrometer (for example, see Patent Literature 1).

This ion mobility spectrometer includes: an ion source 1 for ionizing component molecules in a sample; a drift region 4 which is provided, for example, within a cylindrical housing (not shown), for measuring the ion mobility; and a detector 5 for detecting ions which have traveled through the drift region 4. Additionally, in order to send the ions generated by the ion source 1 into the drift region 4 in a pulsed form with a short duration, a shutter gate 3 is provided at the entrance to the drift region 4. The atmosphere inside of the housing is maintained at atmospheric pressure or low vacuum of approximately 100 Pa. A uniform electric field having a downward potential gradient (for accelerating ions) in the moving direction of the ions (in FIG. 3, the Z-direction) is formed within the drift region 4 by DC voltages respectively applied to a number of ring-shaped electrodes 2a included in a drift-electrode group 2 arranged within the drift region 4. A flow of neutral diffusion gas is formed in the opposite direction to the direction of the acceleration by the electric field.

The ions generated in the ion source 1 are temporarily dammed by the shutter gate 3. The shutter gate 3 is subsequently opened for a short period of time, whereupon the ions in a packet-like form are introduced into the drift region 4. Colliding with the counterflowing diffusion gas within the drift region 4, the introduced ions are driven forward by the accelerating electric field. Those ions are temporally separated according to their ion mobilities, which depend on the size, steric structure, electric charge and other properties of the individual ions. Accordingly, ions with different ion mobilities reach the detector 5 having certain intervals of time. If the electric field within the drift region 4 is uniform, the collision cross-section between an ion and the diffusion gas can be estimated from the drift time required for the ion to pass through the drift region 4.

As the shutter gate 3 for controlling the blockage and passage of the ions, a gate electrode described in Patent Literature 2, Non Patent Literature or other documents is often used, which is generally called the "Bradbury-Nielsen gate". FIG. 4 is a schematic perspective view of a shutter gate employing the Bradbury-Nielsen gate described in Patent Literature 2.

In the shown example, two comb electrodes 231 and 232 created by winding, etching or other appropriate techniques are adhered to one surface of a plate-shaped ceramic base 21 in which a circular opening 22 is formed. One comb electrode 231 is connected to a positive-voltage input terminal 241, and the other comb electrode 232 is connected to a negative-voltage input terminal 242. The resulting electrode system has thin-wire electrode lines stretched over the opening 22, with positive and negative voltages alternately applied to the individual electrode lines aligned in the x-direction. The voltages applied to the two comb electrodes 231 and 232 through the positive and negative voltage input terminals 241 and 242 are controlled to create an ion-damming electric field within an area near the opening 22 or dissolve this electric field to allow ions to freely pass through.

In such an ion mobility spectrometer, if water vapor, solvent droplets or similar particles which have not been fully vaporized are present within the drift region 4, the ions to be subjected to the measurement come in contact with those fine particles. This constitutes a significant factor of the fluctuation of the drift time. Therefore, in order to remove as much as possible such vapor and fine solvent droplets from the drift region 4, the drift tube which forms the drift region 4 is heated to a high temperature during the analysis. In normal cases, the heating temperature is within a range of 120-130° C. Actually, it is more preferable to increase the temperature to higher levels (150-160° C.).

However, exposing the shutter gate having the previously described structure to a high temperature causes the comb electrodes 231 and 232 to be taut or slack due to the difference in the coefficient of thermal expansion between the ceramic base 21 and the metallic comb electrodes 231 and 232. Consequently, for example, the neighboring wire electrodes stretched over the opening 22 may come in contact with each other, making the shutter unable to fully perform its function. Furthermore, the wire electrodes may be deformed or severed, in which case the shutter becomes unusable. Due to such restrictions, it has been necessary to set the temperature of the device at 120-130° C. or lower levels. A measurement with the drift tube heated to a high temperature as mentioned earlier has been impractical.

CITATION LIST

Patent Literature

Patent Literature 1: JP 2005-174619 A
Patent Literature 2: WO 03/065763 A

Non Patent Literature

Non Patent Literature 1: Ignacio A. Zuleta and four other authors. "Micromachined Bradbury-Nielsen Gates", *Analytical Chemistry*, Vol. 79. No. 23, 2007. pp. 9160-9165

SUMMARY OF INVENTION

Technical Problem

The present invention has been developed to solve the previously described problem, and its primary objective is to provide a gate electrode in which a malfunction of the shutter or deformation or failure of the electrodes is less likely to occur even under an environment with a temperature higher than conventional levels, as well as an ion mobility spectrometer which uses such a gate electrode as the shutter gate to sufficiently remove water vapor, solvent droplets or similar particles from the drift region when performing an ion mobility spectrometric analysis.

Solution to Problem

The gate electrode according to the present invention developed for solving the previously described problem is a gate electrode for damming charged particles and allowing the charged particles to pass through by an electric field, including:
 a) a plate-shaped base part made of an insulating material, with a rectangular ion-passing opening formed at the center of the base part;
 b) two conductive fixture parts made of an electrically conductive material, the conductive fixture parts attached to the base part in such a manner as to be substantially parallel to each other along two mutually facing sides on the inside of the rectangular opening of the base part;
 c) two insulating fixture parts made of the same insulating material as the base part, the insulating fixture parts attached to the two conductive fixture parts in such a manner as to be substantially parallel to each other along the two mutually facing sides on the inside of the conductive fixture parts attached to the inside of the rectangular opening of the base part;
 d) a first electrode part including a plurality of parallel conductive wires stretched in such a manner as to extend in a substantially orthogonal direction to the extending direction of the conductive fixture parts and the insulating fixture parts, each of the conductive wires having one end connected to one of the conductive fixture parts and the other end connected to the insulating fixture part arranged opposite to the one of the conductive fixture parts; and
 e) a second electrode part including a plurality of parallel conductive wires stretched substantially parallel to and between the conductive wires constituting the first electrode part, each of the conductive wires of the second electrode parts having one end connected to the other one of the conductive fixture parts and the other end connected to the insulating fixture part arranged opposite to the other one of the conductive fixture parts,
 where the opening width of the rectangular opening in the extending direction of the conductive wires and the width of the conductive fixture parts in the same direction are each determined based on the coefficient of thermal expansion of the material of the base part and the insulating fixture parts, the coefficient of thermal expansion of the material of the conductive fixture parts, as well as the coefficient of thermal expansion of the conductive wires, in such a manner that the amount of change in the distance between each of the conductive fixture parts and a central line of the rectangular opening extending in an orthogonal direction to the extending direction of the conductive wires, and the amount of change in the length of the conductive wires corresponding to that distance, are balanced with each other for a predetermined change in temperature.

The conductive wires which constitute each of the first and second electrode parts may be a comb electrode in which the conductive wires have their respective ends connected to each other by a conductive wire or strip-like element extending in a substantially orthogonal direction to the conductive wires at the positions where the conductive wires are fixed to the conductive fixture part. They may alternatively be linear conductive elements which are separate from each other and have no such connecting part.

An ion mobility spectrometer according to the present invention developed for solving the previously described problem is characterized in that the gate electrode according to the present invention is used as a shutter gate for introducing ions in a packet-like form into a drift region.

In the gate electrode according to the present invention, each of the conductive wires which are stretched over the rectangular opening of the base part has one end connected to one of the conductive fixture parts and the other end connected to one of the insulating fixture parts. This configuration is common to both the first electrode part and the second electrode part. Therefore, it is possible to assume that all conductive wires undergo the same change in length for a change in temperature. Now, consider the case where the conductive wires have both ends connected to the base part. When these conductive wires expand due to a change in temperature, the conductive wires will become taut or slack if the base part does not similarly expand with the conductive wires and widen its opening. If the conductive wires are made of a material whose coefficient of thermal expansion is lower than that of the insulating material which forms the base part, the conductive wires will undergo tensile force with the increase in temperature and may eventually be severed. Conversely, if the conductive wires are made of a material whose coefficient of thermal expansion is higher than that of the insulating material which forms the base part, the conductive wires will become slack with the increase in temperature and may eventually come in contact with each other, causing a short circuit.

By comparison, the gate electrode according to the present invention have the conductive fixture parts attached to the inside of the rectangular opening of the base part. When these conductive fixture parts expand due to an increase in temperature, their expansion occurs toward the inner area of the rectangular opening. In other words, the expansion of the conductive fixture parts occurs in the opposite direction to the widening of the opening caused by the thermal expansion of the base part. Accordingly, with the increase in the temperature, the position of the ends of the conductive wires fixed to the conductive fixture parts moves by an amount that approximately corresponds to the difference between the amount of widening of the rectangular opening and the amount of expansion of the conductive fixture parts toward the inner area of the opening. If the amount of this movement is made to be to some extent equal to the amount of elongation (expansion) of the conductive wires, the degree of tautness or slack of the wires will be reduced.

The material of the base part and the insulating fixture parts, that of the conductive fixture parts, as well as that of the conductive wires each have a specific coefficient of thermal expansion, which is determined by the selection of the material and has certain restrictions. In the configuration of the gate electrode according to the present invention, the width of the rectangular opening and that of the conductive fixture parts in the extending direction of the conductive wires are each appropriately determined under the condition that the coefficients of thermal expansion of those materials have been fixed. The degree of freedom of the adjustment of those geometrical sizes is dramatically higher than that of the selection of the coefficients of thermal expansion of the materials. Therefore, it is possible to adjust those sizes to prevent the conductive wires from being excessively tensioned, or conversely, from being significantly slack due to a thermal expansion even when the temperature is considerably increased.

Advantageous Effects of the Invention

In the gate electrode according to the present invention, the conductive wires which function as electrodes are less likely to become taut or slack due to an increase in temperature. Even under a high-temperature environment, the conductive wires will neither be excessively slack and eventually come in contact with the neighboring wires, nor be excessively tensioned and eventually deformed or severed.

In the ion mobility spectrometer according to the present invention, since the gate electrode with the previously described features is used as the shutter gate, the drift tube (or similar component) can be heated to a higher temperature than in a conventional device. This enables a sufficient removal of water vapor, solvent droplets or similar particles from the drift region and thereby improves the accuracy and resolving power of the ion mobility spectrometry.

DESCRIPTION OF EMBODIMENTS

One embodiment of the gate electrode according to the present invention and the ion mobility spectrometer using the same gate electrode as a shutter gate is hereinafter described with reference to the attached drawings.

Figure 1:
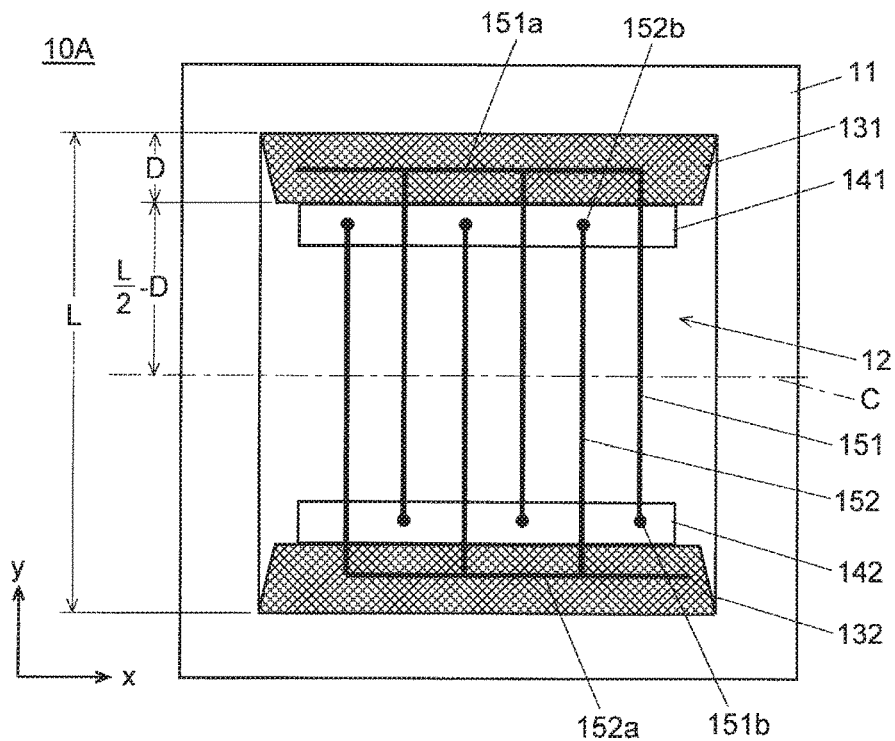
FIG. 1 is a plan view of a gate electrode as one embodiment of the present invention.

FIG. 1 is a plan view of the gate electrode 10A in the present embodiment.

As shown in FIG. 1, the gate electrode 10A in the present embodiment includes a plate-shaped ceramic base 11 having a rectangular outer contour as viewed from above (i.e. when the plane of the paper is viewed from above), with a rectangular opening 12 formed at its center. For convenience, the vertical and horizontal directions in the drawing are defined as the y and x directions, respectively. A pair of conductive fixture members 131 and 132, which are made of metal, identical in size, and trapezoidal in shape as viewed from above, are respectively attached to the two sides facing each other in the y direction on the inside of the rectangular opening 12 (upper and lower sides in FIG. 1). Furthermore, a pair of insulating fixture members 141 and 142, which are made of ceramic and identical in size, are attached to the inner sides of the pair of conductive fixture members 131 and 132, facing each other. Hereinafter, the length of the opening 12 in the y direction is denoted by L, and the width of the conductive fixture members 131 and 132 in the y direction is denoted by D.

In a comb electrode 151, which is one of a pair of comb electrodes, a connecting portion 151a which connects a plurality of thin-wire electrodes that correspond to the comb teeth is adhered to the upper conductive fixture member 131. The distal ends of those thin-wire electrodes are adhered to the lower insulating fixture member 142. Similarly, in the other comb electrode 152, a connecting portion 152a is adhered to the lower conductive fixture member 132, with the distal ends of the thin-wire electrodes (which correspond to the conductive wires in the present invention) adhered to the upper insulating fixture member 141. A conductive adhesive which is sufficiently resistant to heat (preferably, to a temperature of 200° C. or higher) may preferably be used to adhere those elements. The connecting portions 151a and 152a of the comb electrodes 151 and 152 are each adhered at or near the midpoint of the width D of the corresponding conductive fixture member 131 or 132. The distal ends 151b and 152b of the thin-wire electrodes of the comb electrodes 151 and 152 are each adhered at or near the midpoint of the width of the corresponding insulating fixture member 141 or 142. In this example, the space between the lower edge of the upper insulating fixture member 141 and the upper edge of the lower insulating fixture member 142 functions as the effective opening in the y direction through which ions can pass.

The base 11 and the insulating fixture members 141 and 142 are made of the same ceramic material and have the same coefficient of thermal expansion. On the other hand, the conductive fixture members 131 and 132 as well as the comb electrodes 151 and 152 are all made of metal. However, these two groups of components are made of different kinds of metal and differ from each other in the coefficient of thermal expansion. Now, suppose that the ceramic has a coefficient of thermal expansion of $\alpha_C$, metal "A" used for the conductive fixture members 131 and 132 has a coefficient of thermal expansion of $\alpha_A$, and metal "B" used for the comb electrodes 151 and 152 has a coefficient of thermal expansion of $\alpha_B$ for an increase in temperature by T° C. (δT). Since the gate electrode 10A has a vertically symmetrical shape with respect to the central line C extending in the x direction, the thermal expansion which occurs above the central line C is hereinafter considered.

If an increase in temperature occurs, the length of the opening 12 in the y direction increases due to the thermal expansion of the base 11. Meanwhile, the width of the conductive fixture members 131 and 132 in the y direction also increases due to their thermal expansion. Accordingly, the amount of change $\delta_C$ in the length from the central line C to the inner side of the conductive fixture member 131 in the y direction for a T–° C. increase in temperature can be expressed by the following equation (1):

$$\delta_C = \{(\delta T \cdot \alpha_C \cdot (L/2)\} - (\delta T \cdot \alpha_A \cdot D) \qquad (1)$$

In equation (1), the first term is the increase in the size of the opening 12 due to the thermal expansion of the base 11, and the second term is the decrease in the size of the effective ion-passage opening due to the thermal expansion of the conductive fixture member 131.

The amount of change $\delta_B$ in the length of the comb electrodes 151 and 152 in the y direction from the central line C to the adhered portion for the same amount of increase in the temperature can be approximately expressed by the following equation (2):

$$\delta_B = \delta T \cdot \alpha_B \cdot \{(L/2) - D\} \qquad (2)$$

In this equation, neither the amount of change in the dimensions of the insulating fixture members 141 and 142 to which the distal ends 151b and 152b of the thin-wire electrodes of the comb electrodes 151 and 152 are adhered, nor the adhered position of those distal ends is considered. However, such a change will be ignorable if the width of the insulating fixture members 141 and 142 in the y direction is sufficiently small.

The aforementioned amount of change $\delta_C$ can be considered as the amount of change in the adhered position of the comb electrodes 151 and 152 on the conductive fixture members 131 and 132. If this amount of change $\delta_C$ is approximately equal to the amount of change SB in the length of the comb electrodes 151 and 152, the comb electrodes 151 and 152 will neither be taut nor slack even under the increased temperature. Accordingly, the coefficients of thermal expansion of the used materials (i.e. ceramic, metal "A" and metal "B"), length L of the opening 12 of the base 11 in the y direction, and width D of the conductive fixture members 131 and 132 in the y direction are previously determined so that $\delta_C=\delta_B$, i.e. so that equation (3) holds true:

$$\alpha_B\{(L/2)-D\}=\alpha_C \cdot (L/2)-\alpha_A \cdot D \quad (3)$$

Since the coefficients of thermal expansion are determined by the materials, the degree of freedom of their selection is extremely low. Accordingly, length L and width D are additionally determined to satisfy equation (3) after the coefficients of thermal expansion $\alpha_A$, $\alpha_B$ and $\alpha_C$ have been determined through the selection of the ceramic, metal "A" and metal "B".

A specific configuration example is as follows: Alumina is selected as the material for both the base 11 and the insulating fixture members 141 and 142. SUS304 (stainless steel) is selected as the material for the conductive fixture members 131 and 132. Fe-Ni36% (the so-called INVAR®) is selected as the material for the comb electrodes 151 and 152. The coefficients of thermal expansion of these materials are: alumina, 7.2 ppm/° C.; SUS304, 17.3 ppm/° C.; and Fe-Ni36%, 1.2 ppm/C Substituting these values into equation (3), i.e. $\alpha_A=17.3$, $\alpha_B=1.2$ and $\alpha_C=7.2$, gives the following equation:

$$1.2\times\{(L/2)-D\}=7.2\times(L/2)-17.3\times D$$

Solving this equation for L gives a relationship expressed as L=5.4×D. According to this equation, for example, the length of the opening 12 of the base 11 in the y direction should be 54 mm if the width of the conductive fixture members 131 and 132 is 10 mm.

Figure 3:
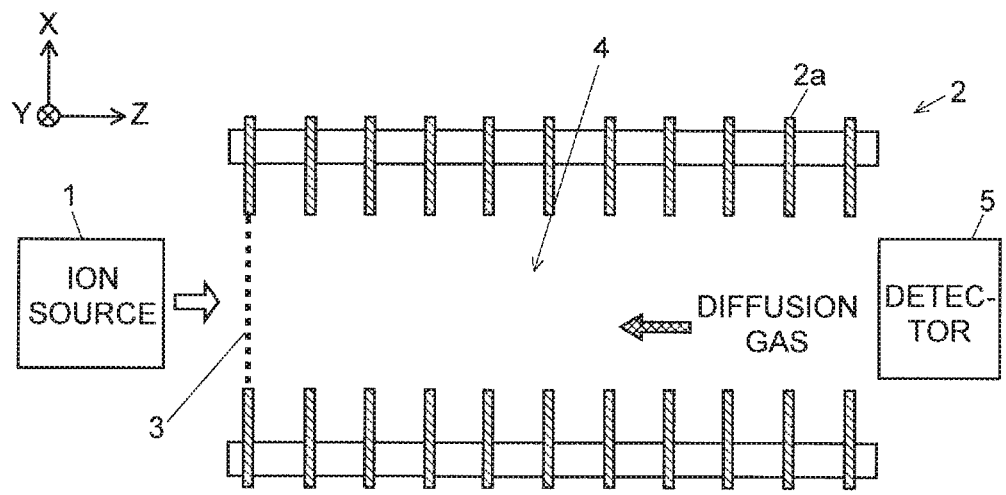
FIG. 3 is a schematic configuration diagram of a common type of ion mobility spectrometer.
Figure 4:
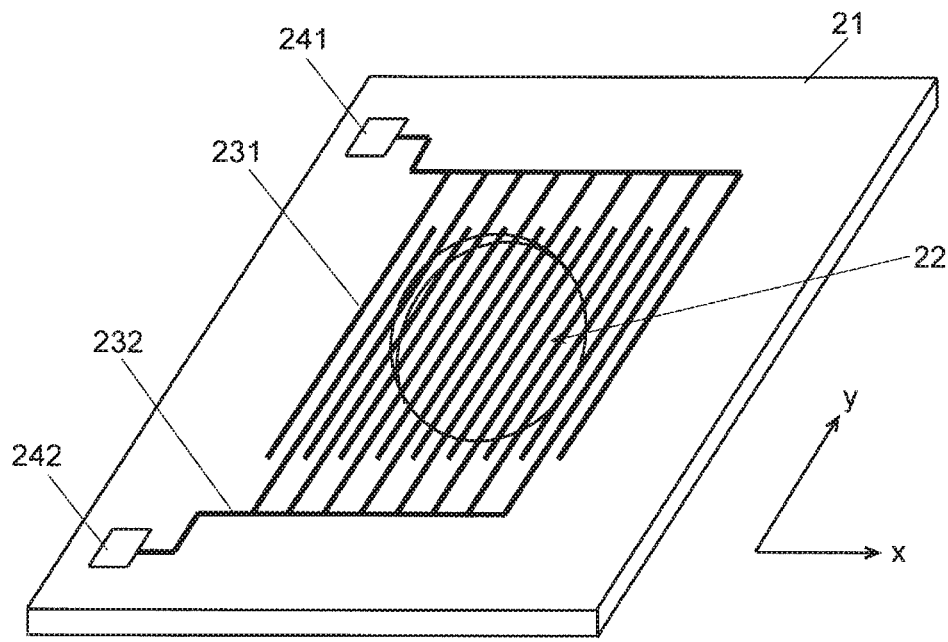
FIG. 4 is a schematic perspective view of one example of the conventional gate electrodes.

The previously described configuration adopted for the gate electrode 10A in the present embodiment makes it possible to prevent the comb electrodes 151 and 152 stretched over the opening 12 from being significantly tensioned, or conversely, from being slack due to an increase in the temperature. The ion mobility spectrometer according to the present embodiment has basically the same configuration as the conventional one shown in FIG. 3 except for the use of the gate electrode 10A as the shutter gate. This allows the drift region to be heated to a higher temperature than conventional levels, without causing the shutter gate to be unable to function as the shutter due to its electrodes being severed or coming in contact with the neighboring electrodes. The use of a higher temperature leads to a greater reduction in the amount of water vapor and solvent droplets in the drift region. This means that the ions introduced into the drift region are less likely to collide with those particles. Consequently, the resolving power and accuracy of the analysis will be improved.

Figure 2:
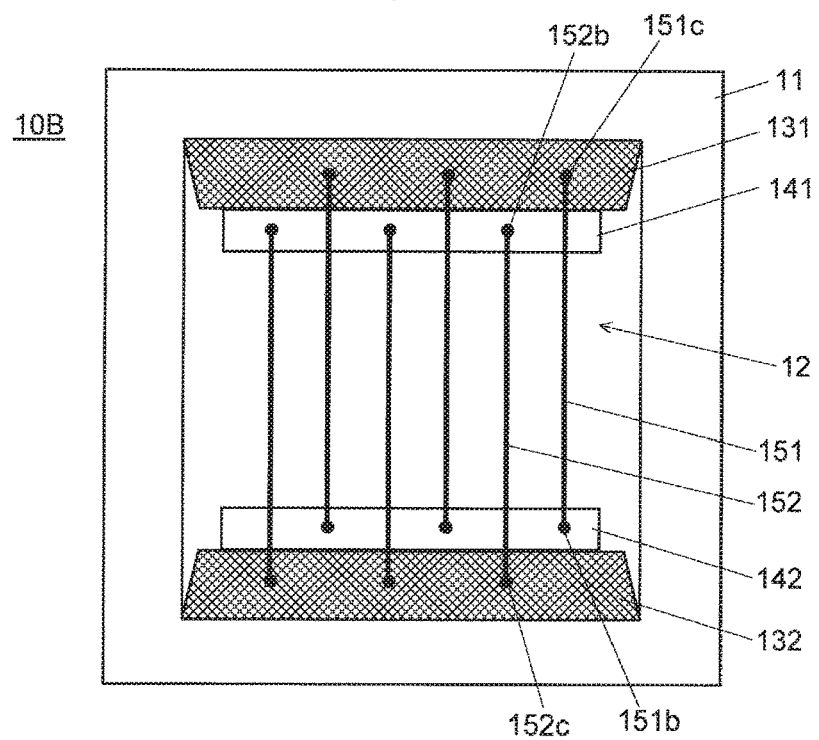
FIG. 2 is a plan view of a modified example of the gate electrode.

The electrodes used in the previous embodiment are comb electrodes having thin-wire electrodes connected to each other by the connecting portion. In place of such comb electrodes, two electrode arrays each of which includes a plurality of metallic wires may be used, as in the gate electrode 10B shown in FIG. 2.

It should be noted that the previous embodiment is a mere example of the present invention, and any change, modification or addition appropriately made within the spirit of the present invention will naturally fall within the scope of claims of the present application.

REFERENCE SIGNS LIST

1 . . . Ion Source
2 . . . Drift-Electrode Group
2a . . . Electrode
3 . . . Shutter Gate
4 . . . Drift Region
5 . . . Detector
10A, 10B . . . Gate Electrode
11 . . . Base
12 . . . Opening
131, 132 . . . Conductive Fixture Member
141, 142 . . . Insulating Fixture Member
151, 152 . . . Comb Electrode
151a. 152a . . . Connecting Portion
151b, 152b . . . Distal End of Thin-Wire Electrode

The invention claimed is:

1. A gate electrode for damming charged particles and allowing the charged particles to pass through by an electric field, comprising:
   a) a plate-shaped base part made of an insulating material, with a rectangular ion-passing opening formed at a center of the base part;
   b) two conductive fixture parts made of an electrically conductive material, the conductive fixture parts attached to the base part in such a manner as to be substantially parallel to each other along two mutually facing sides on an inside of the rectangular opening of the base part;
   c) two insulating fixture parts made of the same insulating material as the base part, the insulating fixture parts attached to the two conductive fixture parts in such a manner as to be substantially parallel to each other along the two mutually facing sides on an inside of the conductive fixture parts attached to the inside of the rectangular opening of the base part;
   d) a first electrode part including a plurality of parallel conductive wires stretched in such a manner as to extend in a substantially orthogonal direction to an extending direction of the conductive fixture parts and the insulating fixture parts, each of the conductive wires having one end connected to one of the conductive fixture parts and another end connected to the insulating fixture part arranged opposite to the one of the conductive fixture parts; and
   e) a second electrode part including a plurality of parallel conductive wires stretched substantially parallel to and between the conductive wires constituting the first electrode part, each of the conductive wires of the second electrode parts having one end connected to another one of the conductive fixture parts and another end connected to the insulating fixture part arranged opposite to the other one of the conductive fixture parts,
   where an opening width of the rectangular opening in the extending direction of the conductive wires and a width of the conductive fixture parts in the same direction are each determined based on a coefficient of thermal expansion of the material of the base part and the insulating fixture parts, a coefficient of thermal expansion of the material of the conductive fixture parts, as well as a coefficient of thermal expansion of the conductive wires, in such a manner that an amount of change in a distance between each of the conductive fixture parts and a central line of the rectangular opening extending in an orthogonal direction to the extending direction of the conductive wires, and an amount of change in a length of the conductive wires corresponding to that distance, are balanced with each other for a predetermined change in temperature.

2. The gate electrode according to claim 1, wherein each of the first and second electrode parts includes a comb electrode in which the plurality of parallel conductive wires have their respective ends connected to each other by a conductive wire or strip-like element extending in a substantially orthogonal direction to the conductive wires.

3. An ion mobility spectrometer, wherein the gate electrode according to claim 1 is used as a shutter gate for introducing ions in a packet-like form into a drift region.

4. An ion mobility spectrometer, wherein the gate electrode according to claim 2 is used as a shutter gate for introducing ions in a packet-like form into a drift region.

* * * * *